(12) United States Patent
Tiano

(10) Patent No.: US 10,188,301 B2
(45) Date of Patent: *Jan. 29, 2019

(54) MEDICAL PROBE AND METHOD OF USING SAME

(71) Applicant: St. Jude Medical, Cardiology Division, Inc., St. Paul, MN (US)

(72) Inventor: Joseph Tiano, Fairfield, CT (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 293 days.

This patent is subject to a terminal disclaimer.

(21) Appl. No.: 14/821,278

(22) Filed: Aug. 7, 2015

(65) Prior Publication Data

US 2015/0342665 A1  Dec. 3, 2015

Related U.S. Application Data

(63) Continuation of application No. 13/540,138, filed on Jul. 2, 2012, now Pat. No. 9,131,853.

(60) Provisional application No. 61/503,743, filed on Jul. 1, 2011.

(51) Int. Cl.
*A61B 5/01* (2006.01)
*A61B 18/12* (2006.01)
(Continued)

(52) U.S. Cl.
CPC .............. *A61B 5/015* (2013.01); *A61B 5/042* (2013.01); *A61B 5/4233* (2013.01);
(Continued)

(58) Field of Classification Search
CPC ....... A61B 5/015; A61B 5/042; A61B 5/4233; A61B 18/1233; A61B 18/1492; A61B 2018/00351; A61B 2018/00357; A61B 2018/00577; A61B 2018/00642; A61B 2018/00666; A61B 2018/00708;
(Continued)

(56) References Cited

U.S. PATENT DOCUMENTS

| 5,343,860 A | 9/1994 | Metzger et al. |
| 5,391,199 A | 2/1995 | Ben-Haim |

(Continued)

FOREIGN PATENT DOCUMENTS

WO  9724983 A2  7/1997

*Primary Examiner* — Devin B Henson
(74) *Attorney, Agent, or Firm* — Wiley Rein LLP

(57) ABSTRACT

The present invention resides in one aspect in a device for monitoring luminal esophageal temperatures in a patient. The device includes a probe adapted to be inserted into an esophagus of the patient. The probe extends between a proximal end and a distal end. A first temperature sensor and a second temperature sensor are coupled to the probe. An electrode is also coupled to the probe. The second temperature sensor is displaced from the first temperature sensor along a longitudinal axis of the probe. A controller processes information received by the electrodes and the temperature sensors. The controller generates a live and continuously updating three dimensional anatomic map and three dimensional thermal map of the esophagus based at least in part on the information received from the temperature sensors and the electrodes. The thermal map and the anatomic map are displayed on a video monitor.

20 Claims, 11 Drawing Sheets

(51) Int. Cl.
*A61B 18/14* (2006.01)
*A61B 5/00* (2006.01)
*A61B 5/042* (2006.01)
*A61B 18/00* (2006.01)

(52) U.S. Cl.
CPC ........ *A61B 5/4848* (2013.01); *A61B 18/1233* (2013.01); *A61B 18/1492* (2013.01); *A61B 2018/00351* (2013.01); *A61B 2018/00357* (2013.01); *A61B 2018/00577* (2013.01); *A61B 2018/00642* (2013.01); *A61B 2018/00666* (2013.01); *A61B 2018/00708* (2013.01); *A61B 2018/00791* (2013.01); *A61B 2018/00797* (2013.01); *A61B 2018/00821* (2013.01); *A61B 2018/00839* (2013.01); *A61B 2018/1467* (2013.01)

(58) Field of Classification Search
CPC ........... A61B 2018/00714; A61B 2018/00791; A61B 2018/00797; A61B 2018/00821
See application file for complete search history.

(56) References Cited

U.S. PATENT DOCUMENTS

| | | |
|---|---|---|
| 5,394,880 A | 3/1995 | Atlee, III |
| 5,546,951 A | 8/1996 | Ben-Haim |
| 5,738,096 A | 4/1998 | Ben-Haim |
| 6,226,542 B1 | 5/2001 | Reisfeld |
| 6,368,285 B1 | 4/2002 | Osadchy et al. |
| 6,650,927 B1 | 11/2003 | Keidar |
| 7,819,817 B2 | 10/2010 | Rahn |
| 9,131,853 B2 * | 9/2015 | Tiano ..................... A61B 5/015 |
| 2006/0106375 A1 | 5/2006 | Werneth et al. |
| 2007/0106287 A1 | 5/2007 | O'Sullivan |
| 2007/0106289 A1 | 5/2007 | O'Sullivan |
| 2008/0177175 A1 | 7/2008 | Mottola et al. |
| 2008/0215047 A1 | 9/2008 | Calabro et al. |
| 2010/0030098 A1 | 2/2010 | Fojtik |
| 2010/0179537 A1 | 7/2010 | Rashidi |
| 2013/0006139 A1 | 1/2013 | Tiano |
| 2014/0012155 A1 * | 1/2014 | Flaherty ................. A61B 5/015 600/549 |

* cited by examiner

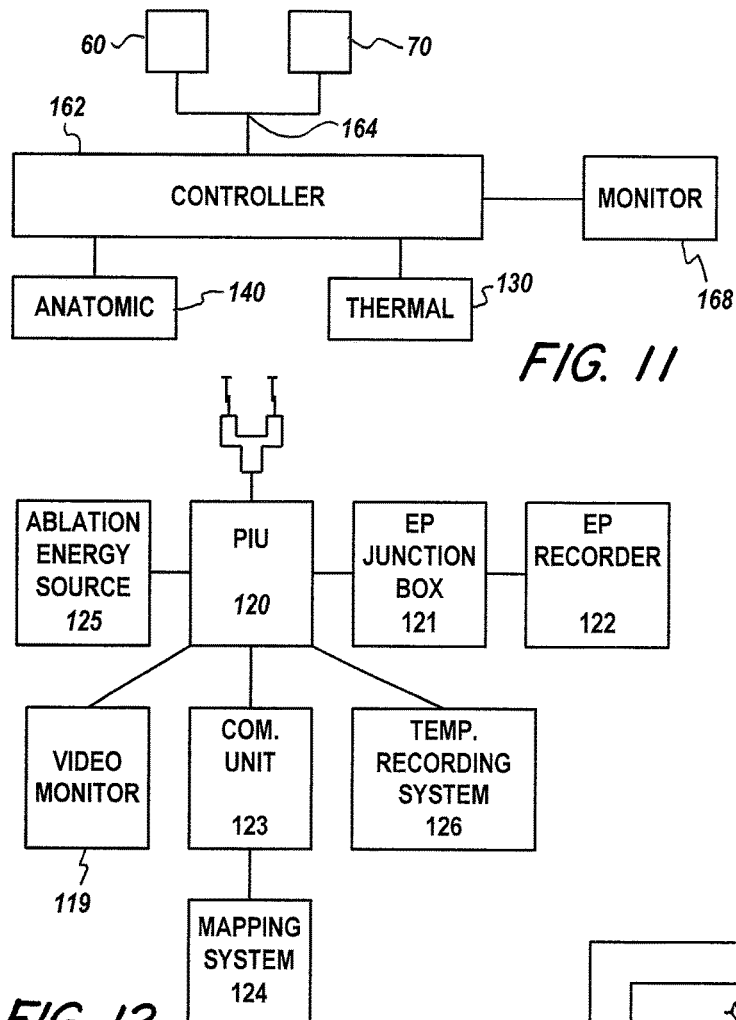
FIG. 11
FIG. 12
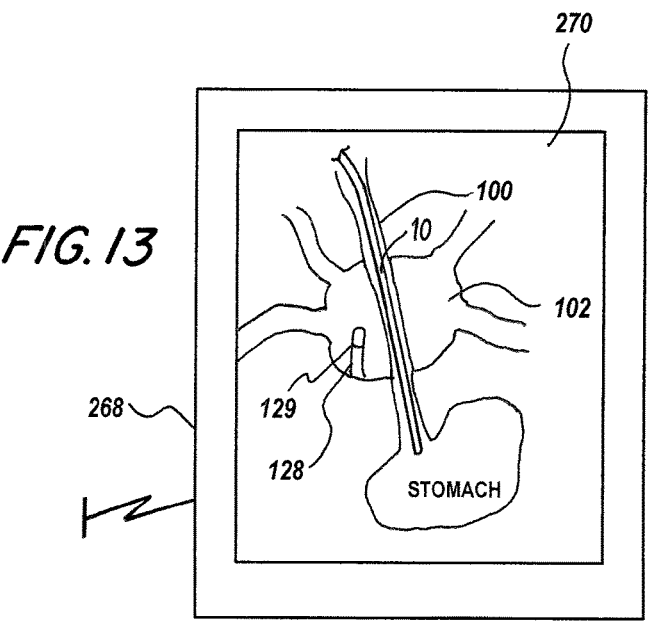
FIG. 13

MEDICAL PROBE AND METHOD OF USING SAME

CROSS-REFERENCE TO RELATED APPLICATIONS

The present application is a continuation of patent application Ser. No. 13/540,138 filed Jul. 2, 2012 which claims the benefit under 35 U.S.C. § 119 (e) of the Provisional Patent Application Ser. No. 61/503,743 filed Jul. 1, 2011, the disclosure of which is incorporated herein by reference in its entirety.

FIELD OF THE INVENTION

The present invention generally relates to a medical probe and a method of using the same. More specifically, the present invention relates to an esophageal probe having one or more temperature sensors and one or more electrodes disposed proximate to a distal end of the probe. The probe allows for continuous, live, and simultaneous esophageal temperature and location monitoring through three dimensional anatomic mapping and three dimensional thermal mapping during an electrophysiology procedure or a surgical procedure.

BACKGROUND OF THE INVENTION

Catheter or electrophysiology ablation is an invasive cardiac procedure that uses radio-frequency (RF) energy or cyroablation to remove faulty electrical pathways from the heart of a person that is prone to developing cardiac arrhythmias such as atrial fibrillation. The procedure involves advancing several flexible catheters through the patient's blood vessels, usually via the femoral vein, internal jugular vein, or subclavian vein. The catheters are advanced into the heart and radio-frequency electrical impulses (or other ablation technique) are used to induce and/or study various arrhythmias, and ablate the abnormal tissue that is causing the arrhythmia, if deemed necessary.

Certain ablation procedures include extensive radiofrequency ablation of the left atrial posterior wall of the heart. Extensive radiofrequency ablation in this location carries the potential risk of collateral damage to structures adjacent to the left atrial posterior wall, including the esophagus. The most worrisome collateral damage is an atrial esophageal fistula, estimated to occur at a rate of approximately 0.5%; however, underreporting is likely, and the true incidence is unknown and could likely be higher. An atrial esophageal fistula is a rare, but almost always a lethal complication.

It is known to insert an esophageal probe into the esophagus of patient undergoing such an ablation procedure. The probe may include one sensor to measure the temperature inside the esophagus. A problem with such known procedures is that there is presently a high rate of esophageal injuries. The ongoing high rate of esophageal thermal injury, despite luminal esophageal temperature (LET) monitoring, is specifically related to the limitations of current techniques and medical devices used for LET monitoring. For example, there is often suboptimal orientation and positioning of the LET probe in relationship to the site of radiofrequency application in the heart, which results in an underestimation of the true LET and leads to esophageal injury due to unseen temperature rises. Current modalities reduce but do not eliminate left atrial-esophageal fistulas.

Esophageal injury is associated with a high mortality rate in addition to numerous co-morbidities. Studies have shown esophageal injury with mucosal changes consistent with thermal injury occurring at a rate as high as 50% after catheter ablation and up to 26% with necrotic and ulcer-like changes. Fistula formation is thought to occur due to conductive heat transfer to the esophagus that causes transmural tissue injury leading to a fistulous connection between the esophageal lumen and the left atrium, leading to sepsis, stroke and eventual death. From several studies, the point of biggest vulnerability for the esophagus to thermal injury from cardiac procedures is during ablation of the posterior left heart chambers, including the left atrium. This is due to its close anatomic position of the esophagus. Unfortunately, there is no clear method to accurately define the precise location of the esophagus. This is compounded by the fact that it is known from cadaveric and imaging studies that the anatomic relationship between the esophagus and left atrium (contact area) varies significantly between individuals and even within the same individual during the course of one procedure, as peristalsis and deglutition promotes esophageal movement.

Knowing that the esophagus is not a static organ and certainly not during a prolonged electrophysiological or surgical procedure there is a need for a medical device to overcome these problems. In addition, the esophagus is often compressed between the left atrium and surrounding structures, causing the esophagus to take a flattened and ovoid shape with a broad contact area to the posterior left atrial wall. Some studies have shown an expected broad contact area that spans the majority of the posterior left atrial wall. Therefore, the esophagus is essentially vulnerable to thermal injury during RF ablation from any location along the posterior left atrial endocardium.

Electroanatomic mapping systems, such as Carto by Biosense Webster and EnSite system by St. Jude Medical, allow a physician to non-fluoroscopically visualize catheters within a three dimensional reconstructed electroanatomic map of the heart that was created by means of intracardiac catheters. These systems are used to accurately visualize intra-cardiac catheters and manipulate them non-fluoroscopically, thereby decreasing radiation exposure to both the operator, patient, and bystander staff. These systems also display activation timing and voltage data to identify arrhythmias. For example, the EnSite system can incorporate and use any standard diagnostic catheter containing an electrode to create an electroanatomic map. The system localizes intra-cardiac catheters and builds a three dimensional map by collecting the electrical points from electrodes on a standard electrophysiology catheter measured within an impedance field created by patches placed on a patient. The EnSite technology is an open platform that is compatible with catheters from most manufacturers and can simultaneously display up to 12 catheters and 64 electrodes.

A three dimensional electro-anatomic shell is created when the intra-cardiac catheter collects various points while in contact with the cardiac endocardium as the physician manipulates the catheter. These points are electrical signals sensed by the electrodes on the catheter. The shell can then be continuously modified throughout the procedure by collecting additional points to decrease the amount of extrapolation and increase accuracy. Methods for creating the above mentioned three dimensional map of the heart are described in U.S. Pat. Nos. 6,226,542, 5,738,096, 5,546,951, 6,368,285, and 6,650,927.

Different strategies have been employed to reduce esophageal thermal injury with various means of monitoring the luminal esophageal temperature or esophageal anatomic location in relation to an intra-cardiac catheter. A disadvantage of these known systems and methods is that they do not provide live visualization of the probe itself within the anatomic shell of the esophagus.

Another disadvantage of known systems and methods is that it has not been possible to non-fluoroscopically visualize the location of a temperature sensor within the esophagus relative to the distal end of an intra-cardiac ablation catheter prior to each ablation, limiting the accuracy of the temperature readings. This problem is compounded because of variability in left atrial and esophageal anatomy, including the esophageal wall thickness.

A temperature sensor for insertion into the esophagus is known from U.S. Pat. No. 7,819,817. A disadvantage of this device is that it does not enable the creation of a live, continuously updating electroanatomic or thermal shell of the esophagus. Another disadvantage of the device disclosed in U.S. Pat. No. 7,819,817 is that it requires a permanent balloon for positioning the probe. The balloon serves to anchor the esophagus in one location and limits natural esophageal mobility; thus, increasing the potential for esophageal injury to that anchored location. A further complication from a balloon includes an increased risk for aspiration by obstructing the natural peristalsis of esophageal and pharyngeal secretions, increasing the risk for a severe pneumonia and respiratory failure. In addition, the balloon can cause great discomfort to the patient both on swallowing and with prolonged inflation during the procedure. The permanent cable and balloon add increased size and stiffness and increases the risk for trauma to the esophageal lumen.

Attempts at localizing the esophagus prior to the catheter ablation procedure have been employed with Magnetic Resonance Imaging (MRI) and Computed Tomography (CT) scans. Unfortunately, studies have shown that despite these imaging modalities being performed within 24 hours of the procedure, there was still significant migration of the esophagus up to 15 mm in less than 24 hours. Thus, imaging the esophagus prior to the procedure is inadequate to locate the true and precise anatomic location of the esophagus.

An esophageal recording/pacing catheter for noninvasively pacing/recording the heart while affixed to an esophageal echocardiography probe is disclosed in U.S. Pat. No. 5,343,860. This device is a planar sheet that was designed solely to be affixed to an esophageal echocardiography probe. Clinical studies have shown that leaving an esophageal echocardiography probe in the esophagus throughout the procedure leads to a higher risk of esophageal-atrial fistulas. It is known that larger probes alter current density from the radiofrequency application in the left atrium and facilitate heating of the esophagus. Thus, it is not recommended to leave a transesophageal probe in the esophagus throughout an atrial fibrillation procedure in its entirety, precluding live and continuous esophageal temperature feedback and live visualization of the probe within the esophagus throughout the procedure.

A large surface area temperature sensing device has been proposed in US Patent Application No. 2010/0030098A1. A disadvantage of this device is that it is solely a temperature-sensing device and does not include any electrodes. In addition, the operator can not visualize this device within the esophagus in real time during the procedure due to the lack of electrodes; thus, precluding live feedback to the operator in regards to the relative distance between the esophageal device and the cardiac ablation catheter.

Attempts at cooling the esophagus have also been proposed, for example in US Patent Application No. 2007/0179537. However, clinical studies have shown that cooling systems are not effective in cooling the deep muscular layers of the esophagus, which are the initial sites of thermal injury in contact with the left atrium and serve as the origin for fistula formation. Thus, the catheter simply cools the exposed surface area of the esophagus, which is not only ineffective in protecting the esophagus but also causes great discomfort to the patient.

Proximity detection systems have been proposed through US Patent Application No. 2007/0106287. This system allows an esophageal catheter to communicate with a cardiac catheter and measure a proximity signal between the two catheters. A disadvantage of the type of system is that there is no direct visualization of the esophagus or atrium via an anatomic or thermal map. Furthermore, proximity is indicated by measured proximity signals, which can be inaccurate secondary to the anatomic variability between the two catheters. In addition, there can be persistent and latent heating up to sixty seconds after termination of ablation. In addition, studies have shown that heating of the esophagus can occur at a distance from an esophageal temperature sensor, as there is great diversity in individual esophageal anatomy. Though two catheters may be far in distance as judged by "proximity signals" there may be significant esophageal anatomy between the two catheters that will conduct the heat from the ablation catheter and promote esophageal injury through conductive heating.

U.S. Patent Application No 2006/0106375 discloses an esophageal catheter that is commercially available today as the EsoPhaStar. A disadvantage of this catheter is that it only provides a static esophageal map. It does not provide live and continuous temperature readings, nor does it allow for concomitant cardiac pacing or sensing or have the capability to create a live three dimensional and continuously updating esophageal thermal map.

SUMMARY OF THE INVENTION

The present invention resides in one aspect in a device for monitoring luminal esophageal temperatures in a patient. The device includes a probe adapted to be inserted into an esophagus. The probe extends between a proximal end and a distal end. A first temperature sensor and a second temperature sensor are coupled to the probe. An electrode is also coupled to the probe. The second temperature sensor is displaced from the first temperature sensor along a longitudinal axis of the probe.

In some embodiments of the present invention the electrode is bracketed by the first temperature sensor and the second temperature sensor along the longitudinal axis of the probe. In some embodiments, the temperature sensors and electrode are proximate to the distal end of the probe. In yet further embodiments, a plurality of electrodes and temperature sensors extend down a length of the longitudinal axis of the probe, wherein the length is selected to enable sufficient temperature monitoring of the esophagus of the patient during a cardiac ablation procedure. In some embodiments, this length is 20 cm and the probe includes at least ten temperature sensors.

In one embodiment of the present invention the distal end of the probe has a J shape to facilitate insertion of the probe into the esophagus. In some embodiments, the flexibility of the probe increases along the longitudinal axis from the proximal end to the J shape at the distal end, and the flexibility of the probe decreases at the J shape so as to substantially retain the J shape during insertion into an esophagus.

In some embodiments of the present invention, the device further includes a temperature sensor interface coupled to the probe. The temperature sensor interface is remote from the distal end of the probe. The temperature sensor interface is in communication with the first temperature sensor and the second temperature sensor. The device further includes an electrode interface coupled to the probe remote from the distal end of the probe, wherein the electrode interface is in communication with at least one of the electrodes.

In some embodiments of the present invention, the device comprises a processor based controller having software executing thereon. The electrode sensor interface is connected to the controller and the controller is adapted receive signals from the electrode sensor interface. The temperature sensor interface is connected to the controller and the controller is adapted receive signals from the temperature sensor interface. A video monitor is in communication with the controller. The controller is configured to display on the monitor an anatomic map of the esophagus based at least in part on the signals received from the electrode sensor interface. The controller is configured to display on the monitor a thermal map of the esophagus based at least in part on the signals received from the temperature sensor interface. In yet further embodiments the thermal map is overlaid on the anatomic map. In some embodiments, the controller is configured to display on the video monitor a position of the probe relative to the anatomic map. In some embodiments of the present invention, the thermal map is displayed in real time and is continuously updated, and the anatomic map is displayed in real time and is continuously updated. In yet further embodiments to the present invention, the probe comprises a location sensor for facilitating detection of the probe.

In some embodiments, the probe comprises a lumen extending between the distal end and the proximal end of the probe. In some embodiments, the lumen is adapted such that a surgeon can introduce an instrument or medicine through the lumen during the procedure. In some embodiments, a fiber optic light is configured to extend through the lumen so as to provide a source of illumination at the distal end of the probe.

The present invention resides in yet another aspect in a system for monitoring the temperature of the esophagus of a patient undergoing an ablation procedure. The system includes a probe adapted to be inserted into an esophagus of the patient. The probe extends between a proximal end and a distal end. A first temperature sensor is coupled proximate to the distal end of the probe, an electrode is coupled proximate to the distal end of the probe, and a second temperature sensor is coupled proximate to the distal end of the probe. The second temperature sensor is displaced from the first temperature sensor along a longitudinal axis of the probe. The system further includes a controller having software executing thereon. The controller is in communication with the first and second temperature sensors and the electrode. A video monitor is in communication with the controller. Software executing on the controller generates an anatomic map based at least in part on information received from the electrode. Software executing on the controller generates a thermal map based at least in part on information received from the temperature sensors. The anatomic map and the thermal map are displayed on the video monitor.

In some embodiments of the present invention, the thermal map is overlaid on the anatomic map on the video monitor. In yet further embodiments of the present invention, the thermal map is displayed in real time and is continuously updated, and the anatomic map is displayed in real time and is continuously updated. In some embodiments the position of the probe is displayed in reference to the anatomic map and the thermal map.

In some embodiments of the present invention an alarm feature is included. Software executing on the controller determines whether a temperature of the esophagus is greater than or equal to a predetermined value. An alarm is triggered when the temperature is greater than or equal to the predetermined value. In some embodiments, an ablation tool is deactivated when the temperature is greater than or equal to the predetermined value.

BRIEF DESCRIPTION OF THE DRAWINGS

FIG. 10 is a diagram of a control system in accordance with one embodiment of the present invention.

FIG. 11 is a diagram of a control system in accordance with one embodiment of the present invention.

FIG. 12 is a diagram of a control system in accordance with one embodiment of the present invention.

FIG. 13 is a video monitor in accordance with one embodiment of the present invention.

DETAILED DESCRIPTION OF THE INVENTION

In general reference to FIGS. 1-9, an esophageal probe 10 in accordance with one embodiment of the present invention is disclosed. It should be noted that although the term probe is used to refer to the medical device disclosed in the present application, it could also be referred to as a catheter or any other term known in the art.

Figure 1:
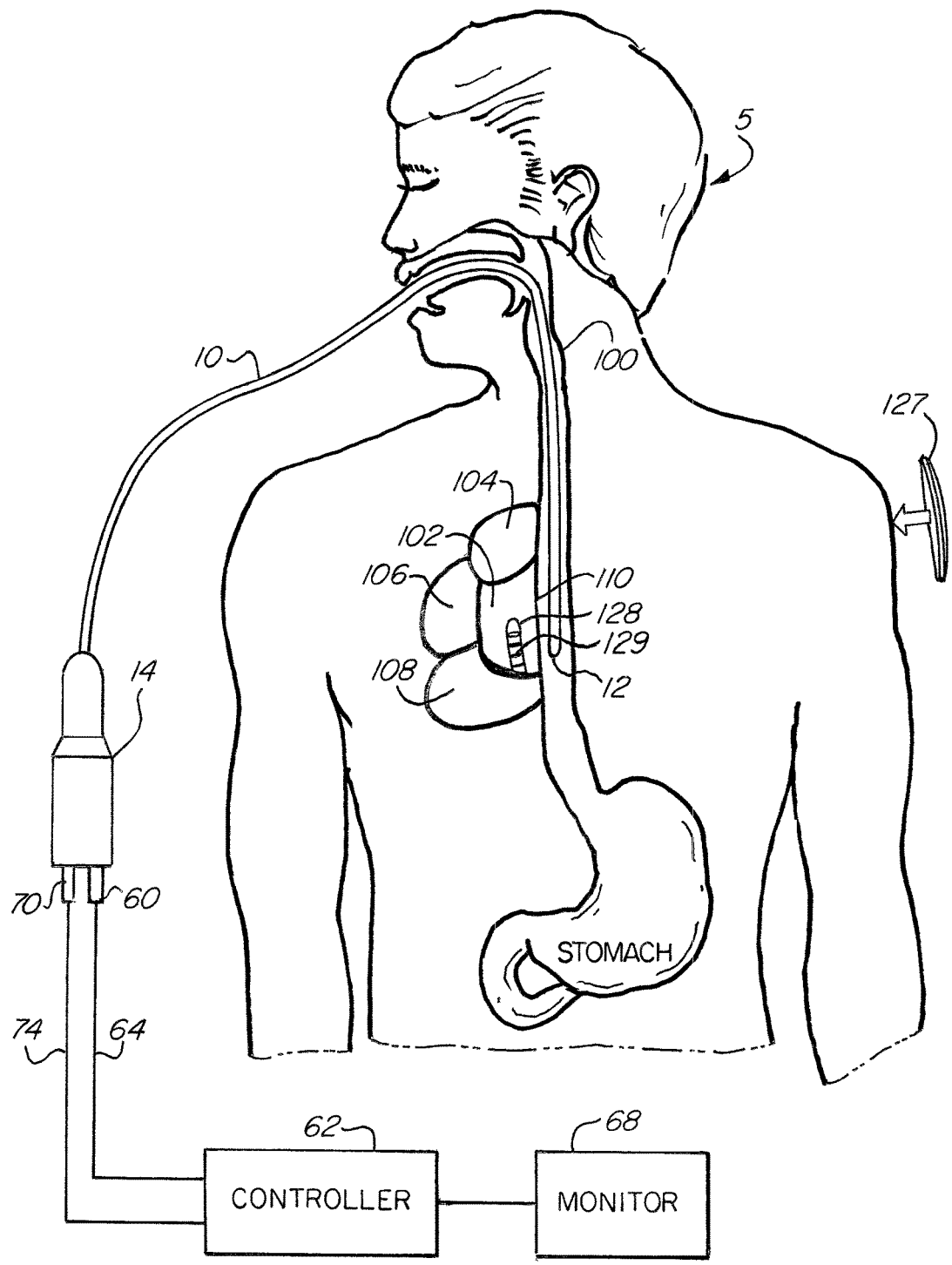
FIG. 1 shows a view of an esophageal probe in accordance with one embodiment of the present invention, wherein the probe is inserted into an esophagus of a patient. The probe is connected to a controller.
Figure 2:
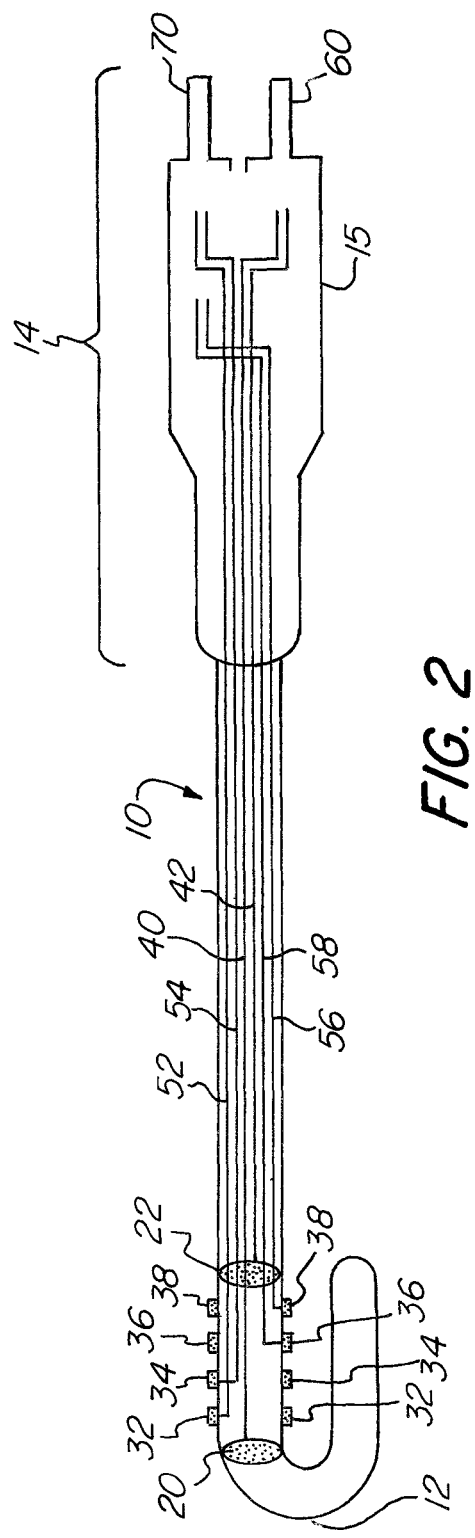
FIG. 2 is a cross-sectional view of a probe in accordance with one embodiment of the present invention.

In reference to FIGS. 1-2, the probe 10 extends along a longitudinal axis between a proximal end 14 and a distal end 12. The probe 10 is adapted so that it can be advanced into a patient's 5 esophagus 100 via oral-pharyngeal or naso-pharyngeal insertion so that the distal end 12 is located proximate to the posterior left cardiac wall 110 and the proximal end 14 is outside the patient's body. The left ventricle 108, the right ventricle 106, the left atrium 102, and the right atrium 104 are shown in FIG. 1. The intra-cardiac catheter 128 with electrodes 129 is also shown in FIG. 1.

In the embodiments shown, the distal end 12 of the probe is formed in the shape of a "J". The J shape facilitates insertion of the probe 10 into the esophagus 100 and minimizes damages to the esophagus and surrounding area caused by insertion of the probe into the esophagus. It should be understood that the present invention is not limited in this regard. For example, the present invention may used without a J shaped distal end, or the distal end may have a different shape. It should also be understood that the probe may have some degree of flexibility that can vary or remain constant along its longitudinal axis. At the same time, the probe may retain sufficient rigidity to retain its shape, but allow for necessary flexing during insertion into and use in the esophagus.

The probe 10 comprises a soft and flexible tube that extends between the proximal end 14 and the J-shaped distal end 12 along the longitudinal axis. In the embodiment shown, the probe is 7 F in diameter with a length of 120 cm; however, other lengths and diameters may be used. The flexible tube is made, at least in part, from a biocompatible material that is known to be safe in the acidic environment of the esophagus 100. In addition, the probe 10 comprises an external coating that is smooth and slippery to allow easy delivery to and comfort in the esophagus 100. The flexibility of the probe 10 increases from the proximal end 14 to the distal end 12 so that the probe 10 is more flexible at the distal end 12 as compared with the proximal end 14 to help make the distal end 12 atraumatic along with its J-shaped design.

In reference to FIGS. 1-9, the probe 10 includes a first temperature sensor 20 and a second temperature sensor 22 coupled to the probe 10 at or proximate to the distal end 12. The first and second temperature sensors 20, 22 are adapted to receive signals indicative of a temperature proximate to the sensor 20, 22. The temperature sensors 20, 22 may be any type of temperature sensor capable of being coupled to the distal end 12 of the probe 10 and being inserted into a cavity of a patient 5. For example, the temperature sensors may include, but are not limited to, a thermistor, a thermocouple, an infrared scanner, and an RTD.

Figure 3:
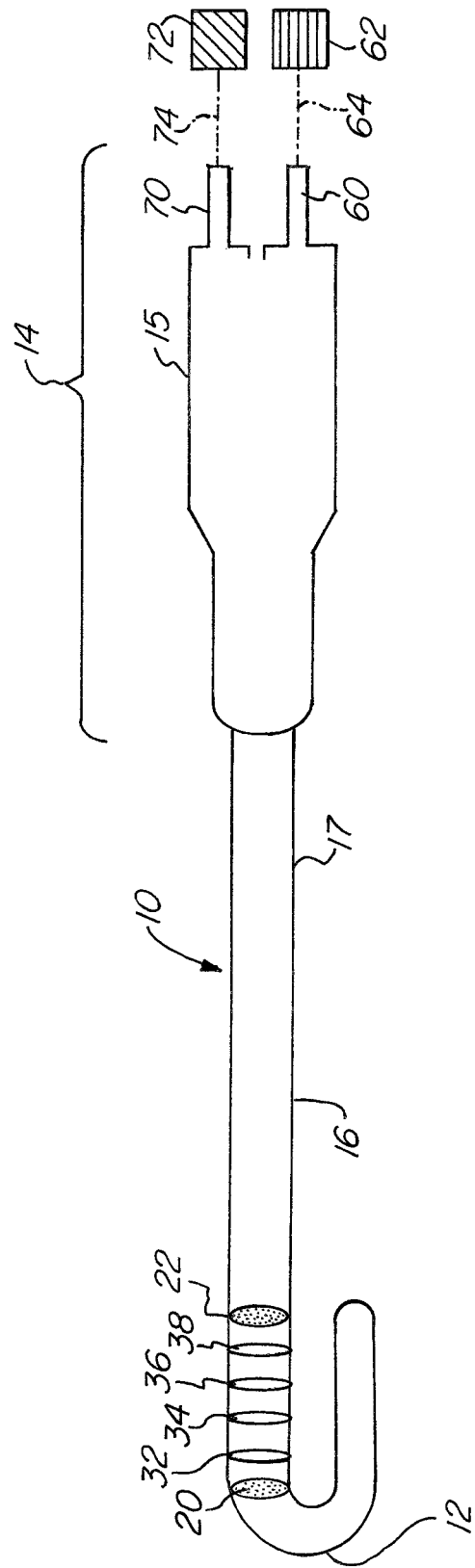
FIG. 3 is a cross-sectional view of the probe shown in FIG. 2.
Figure 4:
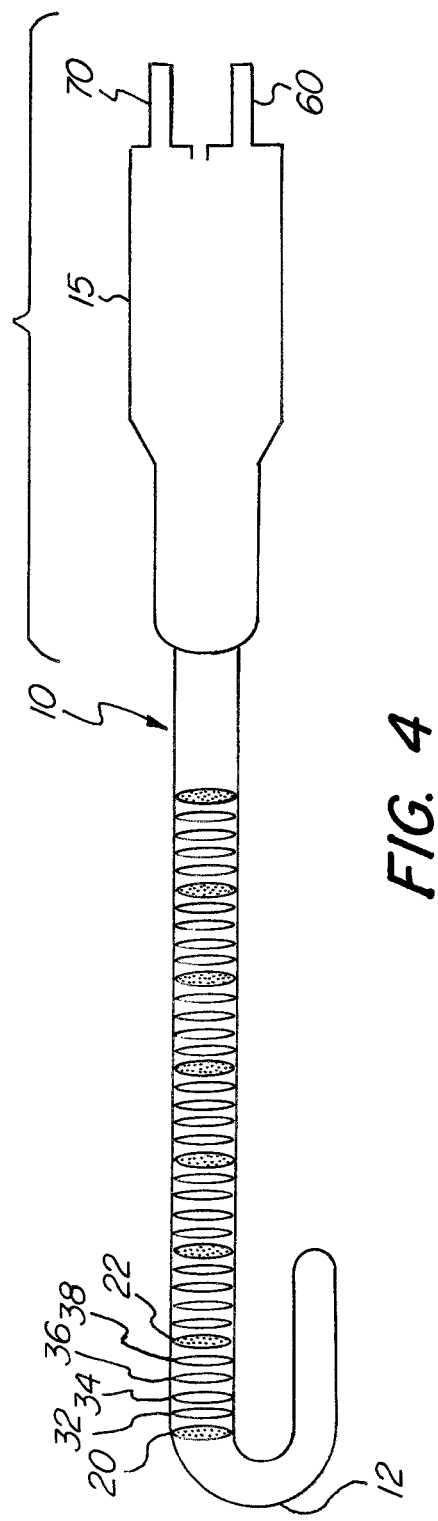
FIG. 4 is a cross-sectional view of a probe in accordance with one embodiment of the present invention.

In reference to FIGS. 2-4, a plurality of electrodes 32, 34, 36, 38 are coupled to the probe 10 at or proximate to the distal end 12. In the embodiment shown, the probe 10 includes four electrodes 32, 34, 36, 38. It should be understood that the number of electrodes may vary. For example, in some embodiments of the present invention a single electrode is coupled to the distal end of the probe, while in other embodiments of the present invention a plurality of electrodes are coupled to the distal end 12 of the probe 10. The plurality of electrodes may extend along a length of the longitudinal axis of the probe in the recurring sequence shown in FIG. 4 and may continue up to approximately 26 cm from the distal tip. In one embodiment, for example, there may be sixty-four electrodes coupled to the probe 10. Each electrode 32, 34, 36, 38 is an annular electrode extending circumferentially around a radial perimeter of the probe 10. The electrodes 32, 34, 36, 38 are flush with the surface of the probe 10. The electrodes 32, 34, 36, 38 are configured to perform electrophysiological measurements as described, for example, in U.S. Pat. No. 5,391,199 or PCT publication WO97/24983, which are incorporated by reference.

In reference to FIGS. 2-4, the plurality of electrodes 32, 34, 36, 38 are bracketed by the first temperature sensor 20 and the second temperature sensor 22 along the longitudinal axis of the probe 10. The temperature sensors 20, 22 and the electrodes 32, 34, 36, 28 are spaced apart along the longitudinal axis of the probe 10. The first temperature sensor 20 is coupled to the probe 10 at or proximate to the distal end 12 of the probe 10. The first electrode 32 is displaced by 2 mm from the first temperature sensor 20 along the longitudinal axis. The second electrode 34 is displaced by 4 mm from the first electrode 32 along the longitudinal axis. The third electrode 36 is displaced by 4 mm from the second electrode 34 along the longitudinal axis. The fourth electrode 38 is displaced by 4 mm from the third electrode 36 along the longitudinal axis, and the second temperature sensor 22 is displaced by 2 mm from the fourth electrode 28 along the longitudinal axis. It should be understood that many spacing variations of the temperature sensors and the electrodes are contemplated and may be used with the present invention, including spacing of one or more temperature sensors in between the electrodes. In a preferred embodiment, the above sequence would be repeated 16 times for a total of 64 electrodes and 20 temperature sensors for a total length of approximately 26 cm.

In reference to FIGS. 2-7, the temperature sensors 20, 22 and the electrodes 32, 34, 36, 28 are in electrical communication with one or more interfaces 60, 70 located at the proximal end 14 of the probe 10. The first temperature sensor 20 is electrically connected to a first connecting wire 40. The first connecting wire 40 extends along the longitudinal axis of the probe 10 and is electrically connected to a first interface 60 located at or proximate to the proximal end 14 of the probe 10. Likewise, the second temperature sensor 22 is electrically connected to a second connecting wire 42. The second connecting wire 42 extends along the longitudinal axis of the probe 10 and is electrically connected to the first interface 60. In reference to FIG. 3, the first interface 60 is connected to a connector cable 64. The connector cable 64 is connected to a controller 62.

In reference to FIGS. 2-7, the electrodes 32, 34, 36, 38 are in electrical communication with interface 70 located at or near the proximal end 14 of the probe 10. Each electrode 32, 34, 36, 38 is connected to a corresponding wire 52, 54, 56, 58 that extends from the respective electrode 32, 34, 36, 38 along the longitudinal axis to the interface 70. The interface 70 is connected to a connector cable 74. The connector cable 74 is connected to a controller 62 for controlling and monitoring each of the electrodes 32, 34, 36, 38.

The controller 62 comprises a processor and software executing thereon. The controller 62 includes software executing thereon for generating an anatomic map of the esophagus based at least in part on signals received from the electrode interface 70. In some embodiments, the software generates the anatomic map based on information received by other sensors, and not the probe 10. In these embodiments, the probe can be visualized by coupling one or more proximity sensors to the probe.

The controller 62 further includes software executing thereon for generating a thermal map of the esophagus based at least in part on the signals received from the temperature sensor interface 60. A video monitor 68 is in communication with the controller 62. The controller 62 is configured to display the anatomic map and the thermal map on the video monitor 68. In this way, it is possible to monitor the position of the probe relative to the esophagus and relative to the heart. It is further possible to monitor temperature gradients within the esophagus and determine how best to conduct the procedure to inhibit injury to the patient.

In some embodiments, the thermal map is overlaid on the anatomic map, providing a convenient user interface. In some embodiments, the anatomic map and the thermal map are displayed in three dimensions. In yet other embodiments, the anatomic map and the thermal map are displayed in two dimensions. In some embodiments, temperature is displayed using color and changes in temperature between one location and a second location indicated by gradient in color. In yet other embodiments, the temperature is displayed numerically.

In reference to FIG. 1, one or more external surface patches 127 (one shown in FIG. 1) is placed on the patient 5. The one or more patches 127 is in communication with the controller 62. Software executing on the controller processes data received from the 10 electrodes 32,34,36,38, intra-cardiac electrodes 129 and surface electrode patches 127 to support generation of the anatomic map. For example, with the EnSite system, the patch would be a surface electrode patch to create and measure impedance differences from the esophageal electrodes 32,34,36,38 and an intra-cardiac catheter's electrodes 129.

In one embodiment of the present invention, software executing on the controller is configured to display on the monitor a position of the probe relative to the anatomic map. The display can be continuously updated during the procedure. In addition, one or more electrodes on the probe can be displayed on the three dimensional esophageal anatomic and thermal maps. This allows an operator to directly visualize the position of the probe and to judge the distance between the esophageal probe 10 and the intra-cardiac radiofrequency ablation (RFA) catheter 128. In addition, this facilitates accurate repositioning of the probe 10 to ensure it is in close proximity to the intra-cardiac RFA catheter 128 for the most accurate temperature readings in the region of the esophagus closest to the intra-cardiac RFA catheter 128. Furthermore, the continuous viewing of the probe 10 through the electrodes 32,34,36,38 alone can serve as a surrogate for the anatomic position of the esophagus 10 if a three dimensional anatomic map is not created of the esophagus 100.

The controller 120 comprises one or more processor based computers having software executing thereon for receiving, analyzing, recording, and displaying data received by one or more sensors coupled to the probe 12. It should be understood that a controller represents any known configuration of controllers, surgical heads, computers, and other supporting equipment known in the art. In reference to FIG. 11, a control system in accordance with one embodiment of the present invention is shown. A controller 162 is in communication with the electrode interface 70 and the temperature interface 60. An anatomic mapping software module 140 is in communication with the controller 162 and a thermal mapping module 130 is in communication with the controller. A video monitor 168 is also in communication with the controller.

An alternative control system is shown in FIG. 12. The system includes a patient interface unit (PIU) 120. The PIU 121 provides a central connection point for varying catheters and electrophysiology equipment. The PIU 120 allows the ablation source 125, electrophysiology recording system 122, mapping system 124, and the temperature monitoring system 126 to be connected and communicate with one another. The PIU 120 in turn is connected to the communications (COM) unit 123 which is then connected to the mapping system 124. The electrical signals and temperature readings collected by the esophageal probe 10 are processed by the anatomic mapping system 124 and electrophysiology recording system 122.

The electrophysiologic (EP) junction box 121 is connected to the PIU 120. The EP junction box 121 is then connected to an electrophysiologic (EP) recording system 122. This system often includes a signal processor (filters, amplifiers), visualization monitor and recording apparatus. Together the electrophysiology junction box 121 and electrophysiology recording system 122 enable the electrical signals from the electrodes 32,34,36,38 on the esophageal probe 10 to be filtered, amplified and displayed as electrograms on the electrophysiology recording system 122.

In reference to FIG. 13, a video monitor 268 in accordance with one embodiment of the present invention is shown. The video monitor displays an anatomic map 270 of the a portion of the heat and a portion of the esophagus. The display in FIG. 13 does not include a thermal map.

In one embodiment, a location sensor can be placed on the distal end of the probe 12, a reference patch 127 on the patient and magnets can be placed below the table to create a magnetic field that will be acquired by a location sensor at the distal end of the probe 12 to allow the probe's compatibility with the CARTO™ mapping system or a comparable system. The location sensor would be tracked within the magnetic field allowing location (x, y, z co-ordinates) as well as orientation (pitch, roll and yaw). The location sensor may be similar to commercially available known sensors such as in the NAVISTAR catheter.

Figure 10:
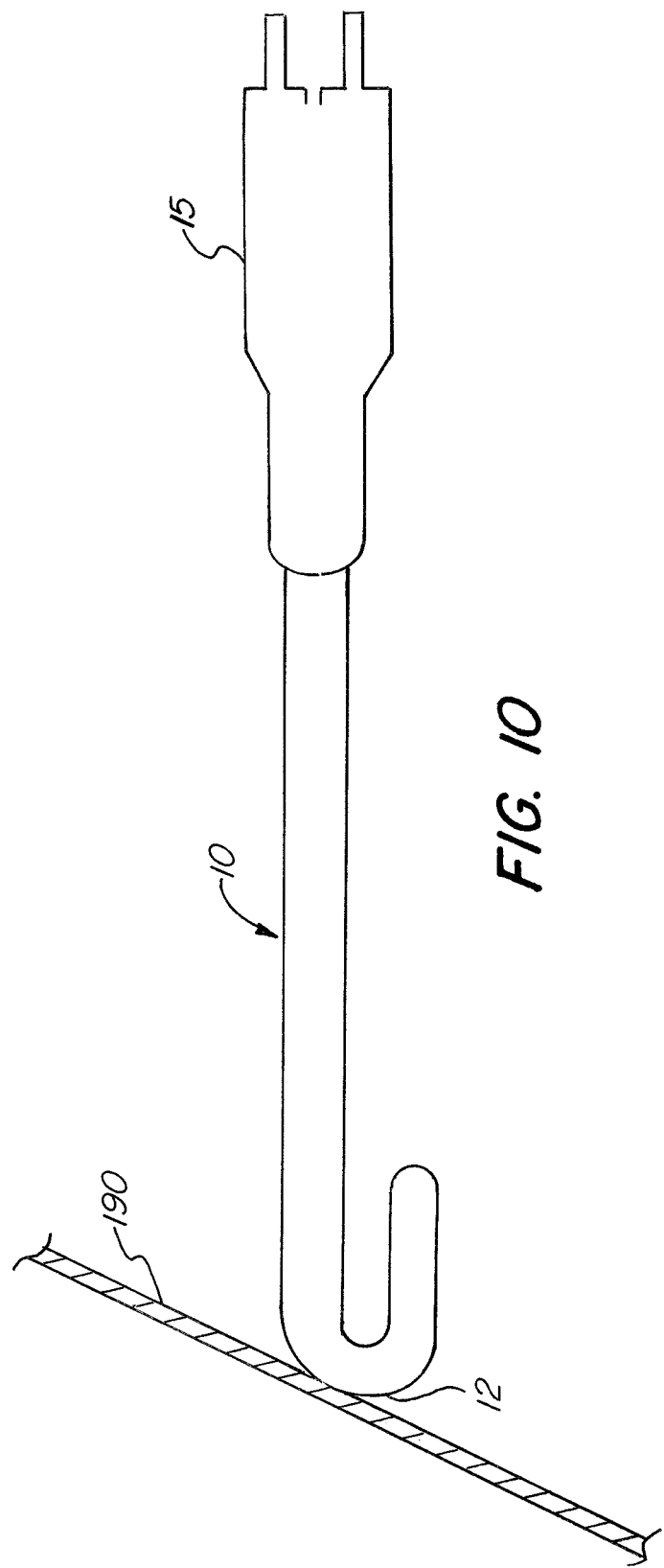
FIG. 10 is a cross-sectional view of the probe shown in FIG. 2.

In reference to FIG. 10, the distal end of the probe 12 is designed in a J-shape to create a blunt end having a rounded outer surface. This design creates an atraumatic tip that is soft and flexible, allowing it to bend and/or flex when it comes into contact with the esophageal lumen 190. When the distal tip 12 flexes against the inner wall 190, it increases the contact surface area with the esophagus 190 and decreases the risk for injury. This design will prevent esophageal perforation or injury to the inner wall of the esophageal lumen 190.

In one embodiment, shown in FIG. 4, twenty temperature sensors 20, 22 are coupled to the probe 10 from a distal to proximal direction. The additional temperature sensors allow for additional temperature data to be recorded along the length of the esophagus, thereby ensuring that the probe is monitoring the portion of the esophagus being subjected to the highest temperature via the ablation. It should be understood that the number of temperature sensors may vary.

Figure 6:
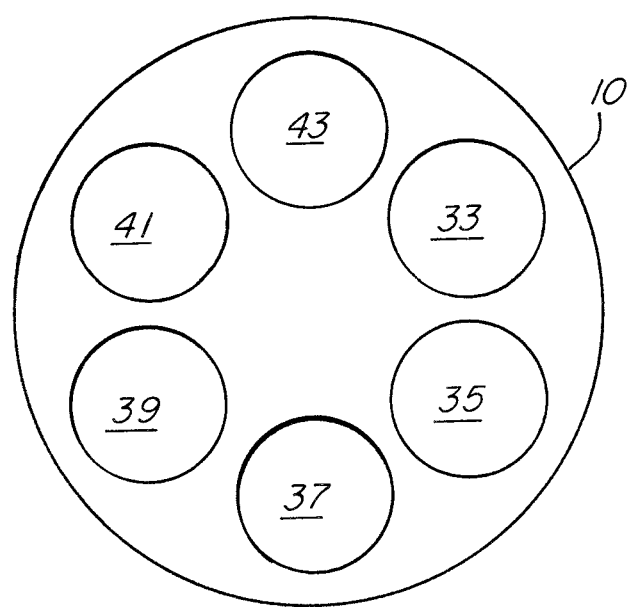
FIG. 6 is a cross-sectional view of the probe shown in FIG. 1.

In reference to FIG. 6, a radial cross section of one embodiment of the probe 10 is shown. The probe 10 includes a plurality of lumen 33, 35, 37, 39, 41, 43 extending between the distal end 12 and the proximal end 14. Each connecting wire 40, 42, 52, 54, 56, 58 passes through its respective and independent lumen 33, 35, 37, 39, 41, 43 extending along the longitudinal axis. The lumen 33, 35, 37, 39, 41, 43 serve to physically and electronically isolate the wires 40, 42, 52, 54, 56, 58 and prevent degradation and distortion of electrical signals passing therethrough. In one embodiment, there is a protective sheath around each lumen. The protective sheath can be made of any suitable material and would be anchored at its distal end to the proximal end of the catheter body 14 by gluing or the like, as would be recognized by one of ordinary skill in the art. It should be understood the present invention is not limited to having an individual lumen for each sensor or electrode.

Figure 5:
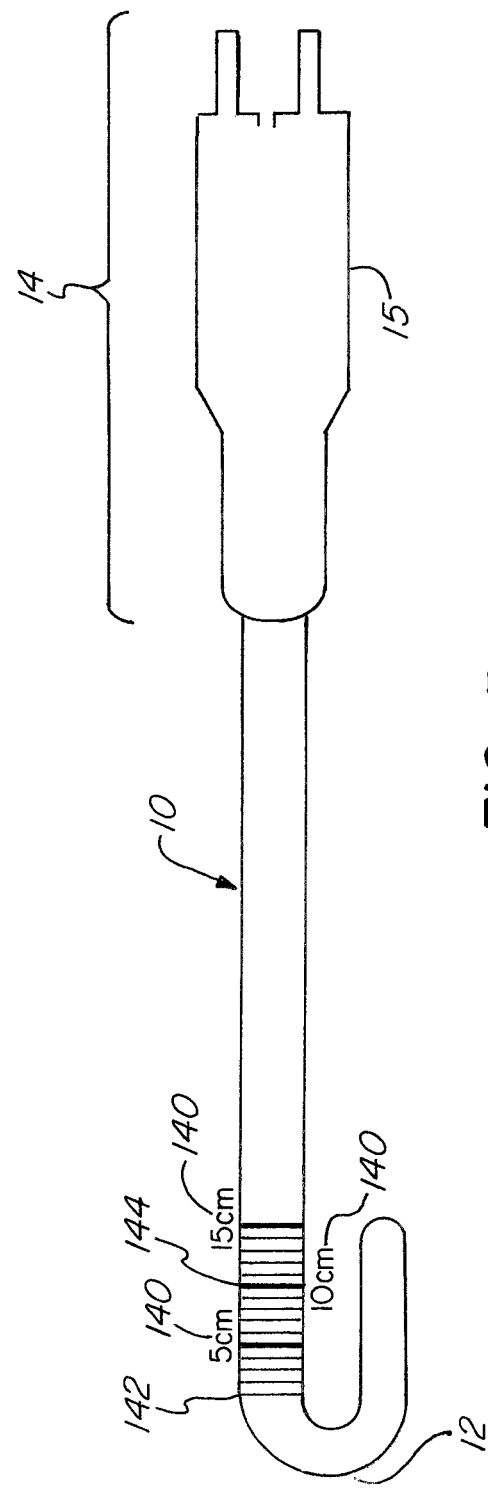
FIG. 5 is a cross-sectional view of a probe in accordance with one embodiment of the present invention.

In reference to FIG. 5, numerical markings 140 are provided on the outside of the probe 10. The marking 140 are provided to assist with positioning the probe within the esophagus 100. The numerical markings 140 on the probe 10 will assist with non-fluoroscopically guided placement by providing feedback as to the depth of the probe 10 within the esophagus 100. The numerical markings 140 will begin at 1 cm at the distal tip 12 and progress to 100 cm near the intermediate to proximal portion 14 of the probe by increments of 1 cm demarcated by single lines 142 with every 5 cm delineated by thick double lines 144, per one embodiment.

Both pacing and sensing can be performed from the electrodes 32,34,36,38 on the esophageal probe 10. This will allow non-fluoroscopic positioning of the probe 10 in the esophagus 100 as guided by the electrograms sensed by the probe 10 from the left atrium 102 or the desired cardiac chamber. Simply put, the closer the probe 10 is to the left atrium 102, the larger the electrograms that will be sensed and displayed by the electrophysiology recording system 122. In addition to non-fluoroscopic means, the radio-opaque electrodes 32,34,36,38 will also be used for fluoroscopic positioning of the probe 10 within the esophagus 100. The pacing capability is beneficial, especially for emergent needs, for example, when the intra-cardiac catheters fail to capture and pace the heart in the setting of asystole or an unstable low heart rate.

Figure 8:
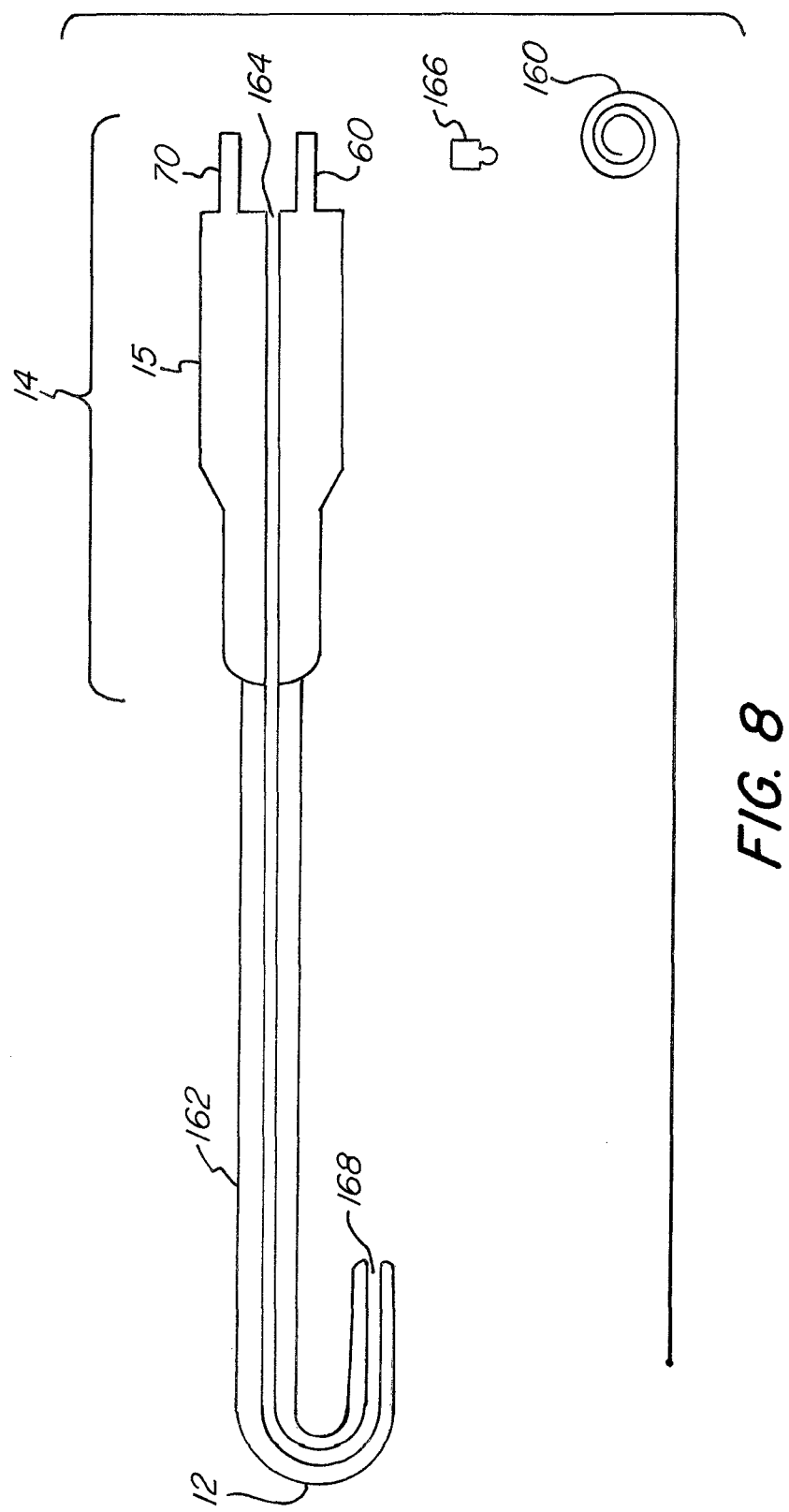
FIG. 8 is a cross-sectional view of a probe in accordance with one embodiment of the present invention including a lumen and stylet receivable therein.

In one embodiment, as shown in FIG. 8, to make insertion easier and to prevent buckling of the probe 10 during intubation of the esophagus 100, a removable stylet 160 is provided that can be inserted into a central lumen 162 of the probe. The central lumen 162 is open at and accessible from the proximal end 14 of the probe so that the stylet 160 can be inserted/removed from the central lumen 162. In the embodiment shown, the stylet 160 is made of a biocompatible, nonreactive material. In one embodiment, when the stylet 160 is withdrawn, the central lumen 162 will remain open and can either be sealed with a plug 166 or other adaptable technique.

In another embodiment, there are two interchangeable stylets 160. The first stylet is stiffer as to facilitate intubation of the esophagus 100 and positioning of the probe 10. The second stylet (not shown in the Figures) is more pliable and softer, its role is to maintain patency and occupy the central lumen 162 after the stiffer stylet is removed. Both stylets when properly positioned in the central lumen 162 are flush with the outer surface of the probe 10 at the distal end 12 of the probe 10 so as to maintain a continuous and smooth surface at the opening 168 of the central lumen at the distal tip. Although the embodiment shown in FIG. 8 includes a stylet, the present invention is limited in this regard, as the present invention can be practiced using a probe without a stylet. In addition, both stylets may be removed allowing for injection of fluids or radiopaque dye, for example barium, through the lumen 162 and into the esophagus 100. Barium is radiopaque and may be injected through the lumen of the probe 162 to visualize the esophagus 100 fluoroscopically.

Each individual temperature sensor 20,22 is capable of collecting independent temperature readings. Thus, when the probe 10 is properly positioned within the esophagus 100, each temperature sensor will provide live and continuous temperature readings representing multiple segments of the esophagus 100. More importantly, thermal rises in individual segments of the esophagus 100 will be captured and displayed visually with color changes coinciding with temperature changes, either rises/falls or steady states. In addition, the operator can program various alert signals including flashing colors, audible sounds, or tactile alerts.

In one embodiment, the thermal map is created by first recording baseline temperatures from the numerous sensors 20, 22 prior to any ablation. Software executing on the controller generates a baseline esophageal thermal map in which the baseline temperatures are color-coded. Following this, during ablations, any temperature change measured by a sensor 20, 22 will be compared to its individual baseline temperature. The difference in temperature will then be processed by the software and will be displayed on the three dimensional thermal map as a color change. In addition, any change in temperature will also be displayed in a blinking manner as to alert the operator as to which specific segment of the esophagus 100 is experiencing a temperature change and which remains at steady state.

Blinking alerts can be programmed to be concordant with the acuity of the rise in temperature; i.e., the faster the rise—the faster the blinking. The thermal map can also be set up to either display individual colors to their respective sensors or to blend a continuous shell of colors, showing general 'hot' zones. The system will also have the ability to display actual temperature readings in numerical values along the three dimensional anatomic map if a thermal map is not preferred by the operator. Finally, the three dimensional thermal map does not require numerous temperature sensors to be created, the thermal map could be created by means of only three temperature sensors positioned at the distal 12, middle 16 and proximal 17 portions of the probe's shaft as seen in FIG. 3, or the thermal map may be created by only two temperature sensors. Overall, the three dimensional, live and continuously updating feature of the thermal map is critical to avoiding thermal injury to the esophagus, as the esophagus is not a static organ.

Figure 9:
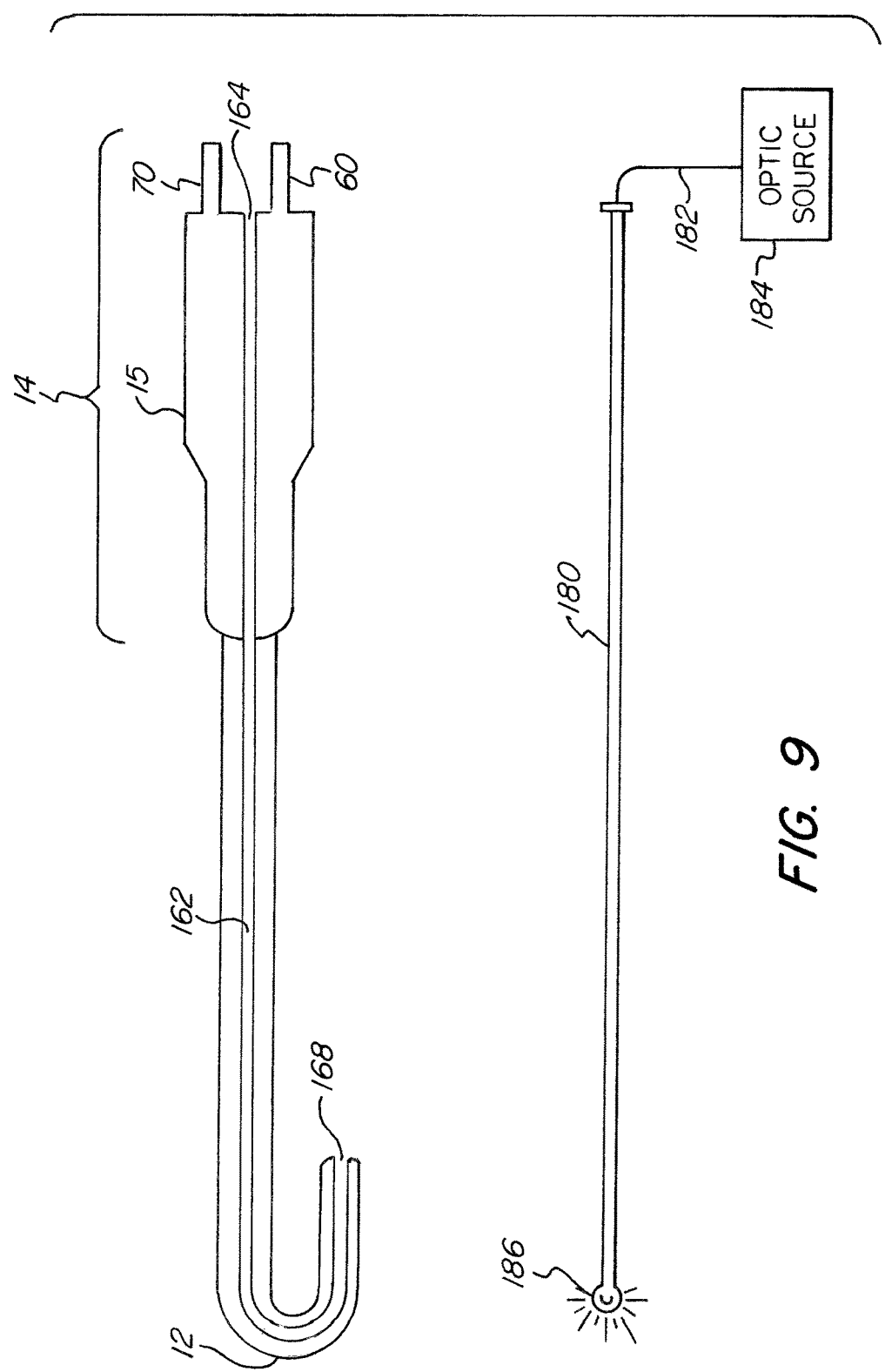
FIG. 9 is a cross-sectional view of a probe in accordance with one embodiment of the present invention including a lumen and fiber optic light receivable therein.

In one embodiment, there is a removable lighted catheter 180 that is interchangeable with the stylet 160 and can be advanced to the distal tip 168 of the distal end 12 of the probe 10 as shown in FIG. 9. The lighted catheter 180 is connected to a cable 182 outside the patient that is then in turn connected to a console 184 outside the body. The lighted catheter can be placed into the central lumen 162 of the probe 10 by the opening 164 in the handle 15 and travel to the distal tip 168 of the distal probe. The lighted catheter 180 when fully positioned is flush at the distal probe tip 168 with the probe itself, providing a smooth and continuous surface. The console 184 comprises of a light source that will transmit light through the cable 182 to the distal lighted catheter tip 186. In some embodiments, the lighted catheter 180 may comprises a fiber optic light. The tip 186 is adapted to encase a light-emitting source. The light source provides visible light only, with infrared and ultra-violet filtered either at the source or in the probe itself, as to prevent damage to the surrounding tissue of the esophagus.

Figure 7:
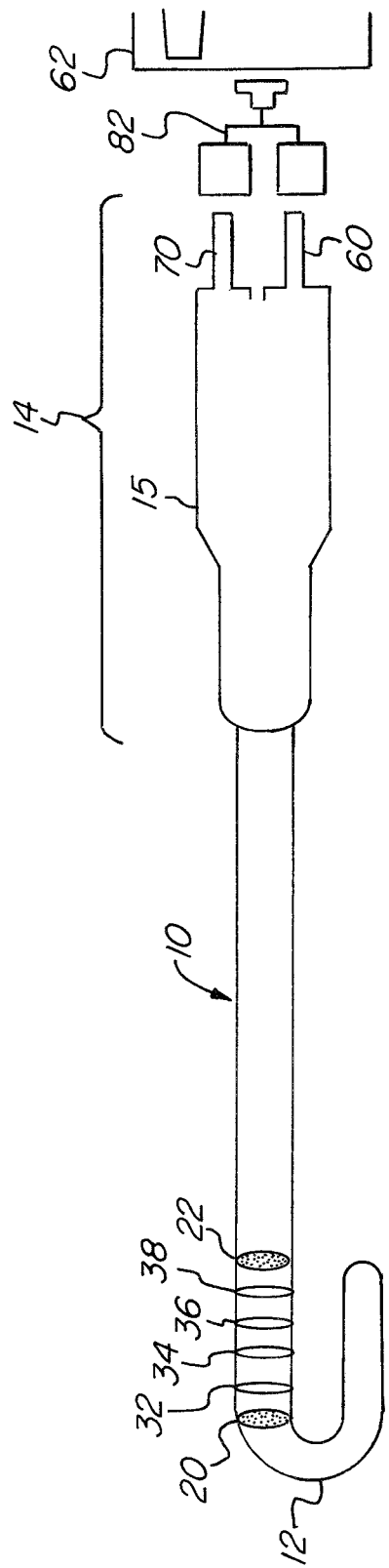
FIG. 7 is a cross-sectional view of the probe shown in FIG. 2.

In one embodiment of the present invention, as shown in FIG. 7, a Y-adaptor 82 is provided. The Y-adaptor 82 connects first interface 60 and second interface 70 with controller 62. In one embodiment of the present invention, software is provided to facilitate compatibility between the probe and the currently available electroanatomic mapping systems if a Y-adaptor 82 is used to create a single control head 80, such as an electroanatomic mapping system 124. The software allows compatibility for simultaneously processing and displaying the three dimensional thermal map on an electroanatomic mapping system. The software enables all information from the temperature sensors 20, 22 and/or the plurality of electrodes 32, 34, 36, 38 on the probe 10 to be displayed by the electroanatomic mapping system, rather than using separate systems to analyze and display temperature readings, electrophysiologic data and three dimensional anatomic maps. In addition, the software enables changes in the luminal esophageal temperature to be simultaneously displayed in numerical fashion on the same control head 80 with the three dimensional electroanatomic map of the heart, thereby, alerting the operator of any changes in the luminal esophageal temperature during radiofrequency ablation.

In some embodiments, the software executing on the controller allows different alarms to be triggered if one or more of the temperatures is equal to or exceeds a predetermined value. The operator of the system may set the predetermined value. The alarm features can be personalized by the operator and the software has the ability to store these predetermined settings for future procedures. The alarm may include both an audible, visual and tactile alert system. The visual alerts provided by the software are described above. In addition, the software will allow the alarm to trigger an automatic shut-off feature on the ablation catheter and ablation source 125, thereby allowing immediate termination of thermal heating via the ablation catheter.

In some embodiments, the esophageal probe is unique in that it is compatible with, but not limited to, the two commercially available electroanatomic mapping systems. The compatibility of the with these and other systems is of particular advantage because does not require a new control head or other equipment, but rather is compatible with existing hardware and software. It can be used during a procedure in conjunction with any intra-cardiac ablation catheter or intra-cardiac diagnostic catheter with electrodes. This enables the three dimensional electroanatomic and thermal maps of the esophagus along with temperature readings and visualization of the electrodes on the probe to be displayed simultaneously on the map with the electroanatomic map of the left atrium.

It should be understood that the disclosed device maybe deployed in many different embodiments with many different procedures, and is not limited to the specific configuration disclosed herein, or the specific esophageal/cardiovascular procedure disclosed herein. For example, in some embodiments, the probe is deflectable, thereby allowing the operator to deflect the distal end 12 with a control located near the proximal end 14. In other embodiments, a contact sensor is incorporated proximate to the distal end of the probe 12. In yet further embodiments of the present invention, a balloon is coupled at the distal end 12. In some embodiments, the probe may be used in cardiothoracic surgery. In yet other embodiments, the probe may be used in cyroablation procedures. In yet further embodiments, the probe may be used in hypothermia or hyperthermia protocols.

Software executing on the controller receives information from the temperature sensors and generates a thermal map of the esophagus. The multitude of temperature sensors mark points along the esophageal electroanatomic map that correlate to varying temperatures. The temperatures and gradients are color coded as to create a live and continuously updating three dimensional color-thermal map of the esophagus. Heating of the esophageal lumen and external esophagus near the left atrium is not linear. There can be temperature stacking after numerous ablations to one location that can only be detected after there is a sudden rise in LET. The three dimensional thermal map shows the gradual heating over a broad anatomic location, letting the operator know of a slow build up of temperature. This function may be turned off as some operators may prefer only an esophageal electroanatomic map with individual temperature readings displayed numerically in real-time alongside the esophagus or on a separate display system. Furthermore, having multiple temperature sensors can help obviate the need for constant repositioning of the probe in conscious sedation patients.

Upon initial intubation of the esophagus, the probe will be slowly withdrawn and maneuvered in varying directions within the esophagus to collect live data points that will be used to construct the three dimensional electroanatomic and thermal maps in conjunction with an electroanatomic mapping and electrophysiology recording systems. This maneuver of collecting data points will be continuously repeated throughout the procedure as to continuously update the three dimensional anatomic and thermal maps, especially since clinical studies have shown that the esophagus is not a static organ and requires vigilant updating for complete accuracy. It should be understood that although esophageal insertion procedures are discussed herein, the present invention is not so limited.

An additional use for the probe will be for research purposes. The probe will provide comprehensive data into the characteristics and mechanisms of esophageal heating during radiofrequency ablation procedures either by endovascular or surgical approaches. Hopefully, the probe will further delineate the pathology involved in the formation of fistulas through future prospective studies.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A system for monitoring luminal esophageal temperatures in a patient, comprising:
    a probe adapted to be inserted into an esophagus of the patient, the probe extending between a proximal end and a distal end;
    a plurality of electrodes and a plurality of temperature sensors extending along a length of the probe to enable continuous monitoring of temperatures in an area of the esophagus subject to formation of atrial-esophageal fistulas during a cardiac ablation;
    a controller having software executing thereon;
    a temperature sensor interface coupled to the probe remote from the distal end of the probe, the temperature sensor interface being in communication with the plurality of temperature sensors;
    an electrode interface coupled to the probe remote from the distal end of the probe, the electrode interface being in communication with the plurality of electrodes;
    wherein the electrode interface is connected to the controller and the controller is adapted to receive signals from the electrode interface;
    wherein the temperature sensor interface is connected to the controller and the controller is adapted to receive signals from the temperature sensor interface;
    a video monitor in communication with the controller;
    wherein the controller is configured to display on the monitor an anatomic map of the esophagus based at least in part on the signals received from the electrode interface;
    wherein the controller is configured to display on the monitor a thermal map of the esophagus based at least in part on the signals received from the temperature sensor interface; and
    wherein the thermal map is overlaid on the anatomic map.

2. The system of claim 1, wherein at least a portion of a heart and at least a portion of the esophagus are displayed on the video monitor.

3. The system of claim 2, wherein the anatomic map of at least a portion of the heart is based at least in part on signals received from an intra-cardiac catheter.

4. The system of claim 1, wherein the controller is configured to display on the monitor a position of at least one of the temperature sensors relative to the anatomic map.

5. The system of claim 4, wherein the thermal map is displayed in real time and is continuously updated, and wherein the anatomic map is displayed in real time and is continuously updated.

6. The system of claim 5 wherein the length along which the plurality of electrodes and the plurality of temperature sensors extend is at least 10 centimeters.

7. The system of claim 1, wherein the controller is configured to display on the monitor a position of the probe relative to the anatomic map.

8. The system of claim 7, wherein the probe further comprises a location sensor for facilitating detection of the probe.

9. The system of claim 8, further comprising a central lumen extending between the distal end and the proximal end.

10. The system of claim 9, further comprising a fiber optic light, wherein the fiber optic light is configured to extend through the central lumen.

11. The system of claim 7, wherein the controller triggers an alarm when the temperature of the esophagus is greater than or equal to a predetermined value.

12. The system of claim 11, wherein an ablation instrument is deactivated when the temperature of the esophagus is greater than or equal to the predetermined value.

13. The system of claim 7, wherein the controller triggers an alarm when the temperature of the esophagus is lesser than or equal to a predetermined value.

14. The system of claim 13, wherein an ablation instrument is deactivated when the temperature of the esophagus is lesser than or equal to the predetermined value.

15. The system of claim 1, wherein the thermal map comprises temperature data received from each of the temperature sensors.

16. The system of claim 15, wherein the thermal data for each sensor is displayed at a position corresponding to the location of that sensor.

17. The system of claim 16, wherein the thermal map of the esophagus is displayed using a plurality of colors.

18. The system of claim 17, wherein a difference in temperature in first location relative to a second location is indicated by a gradient in color.

19. The system of claim 16, wherein numeric temperatures values are overlaid on the thermal map.

20. A system for monitoring luminal esophageal temperatures in a patient, comprising:
a probe adapted to be inserted into an esophagus of the patient, the probe extending between a proximal end and a distal end, the probe comprising a plurality of electrodes and a plurality of temperature sensors extending along a length of the probe to enable continuous monitoring of temperatures in an area of the esophagus subject to formation of atrial-esophageal fistulas during a cardiac ablation;
a controller having software executing thereon;
a video monitor in communication with the controller;
wherein the controller is configured to display on the monitor an anatomic map of the esophagus based at least in part on data received from the plurality of electrodes;
wherein the controller is configured to display on the monitor a thermal map of the esophagus based at least in part on data received from the plurality of temperatures sensors; and
wherein the thermal map is overlaid on the anatomic map.

* * * * *